(12) United States Patent
Frimberger

(10) Patent No.: US 6,319,287 B1
(45) Date of Patent: Nov. 20, 2001

(54) STENT ASSEMBLY

(75) Inventor: Eckart Frimberger, München (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 09/546,324

(22) Filed: Apr. 7, 2000

(30) Foreign Application Priority Data

Apr. 9, 1999 (DE) .............................................. 199 16 060

(51) Int. Cl.[7] .................................................... A61F 2/00
(52) U.S. Cl. ...................... 623/23.64; 623/1.11; 623/1.23
(58) Field of Search ................................. 623/1.11, 1.23, 623/23.64, 23.65, 23.66, 23.7

(56) References Cited

U.S. PATENT DOCUMENTS

| | | | |
|---|---|---|---|
| 4,963,129 | | 10/1990 | Rusch . |
| 5,713,948 | * | 2/1998 | Uflacker ................................ 623/1.11 |
| 6,019,779 | * | 2/2000 | Thorud ................................ 623/1.11 |
| 6,068,654 | * | 5/2000 | Berg ..................................... 623/1.11 |
| 6,132,450 | * | 10/2000 | Hanson ................................ 623/1.11 |
| 6,132,471 | * | 10/2000 | Johlin .................................. 623/1.11 |
| 6,214,036 | * | 4/2001 | Letendre ............................. 623/1.11 |
| 6,221,096 | * | 4/2001 | Aiba .................................... 623/1.11 |
| 6,241,738 | * | 6/2001 | Dereume ............................. 623/1.11 |

FOREIGN PATENT DOCUMENTS 42 33 514 C    4/1994  (DE) .

* cited by examiner

*Primary Examiner*—Michael J. Milano
(74) *Attorney, Agent, or Firm*—Diller, Ramik & Wight

(57) ABSTRACT

The stent assembly comprises a tubular stent and a pusher hose for advancing the stent. A guiding string may be pushed through the stent and the pusher hose. For coupling the stent to the pusher hose, the stent is provided with a filament that may be placed in a laterally open receptacle in the pusher hose where it is blocked by the guiding string. On the guiding string, the stent is placed in a body channel, it being possible to advance or pull back the stent. After the correct position has been reached, the guiding string is pulled out and the pusher hose is removed. The filament is accessible to an extraction tool if the stent should be pulled out or changed in position posteriorly.

6 Claims, 2 Drawing Sheets

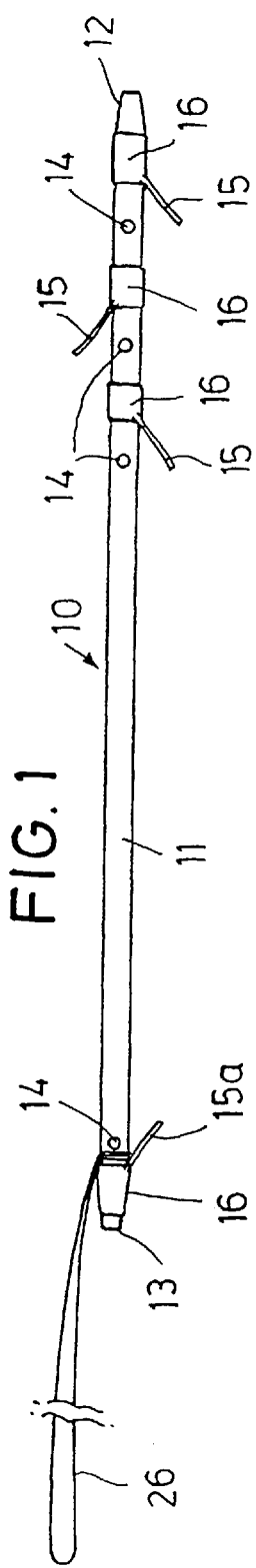
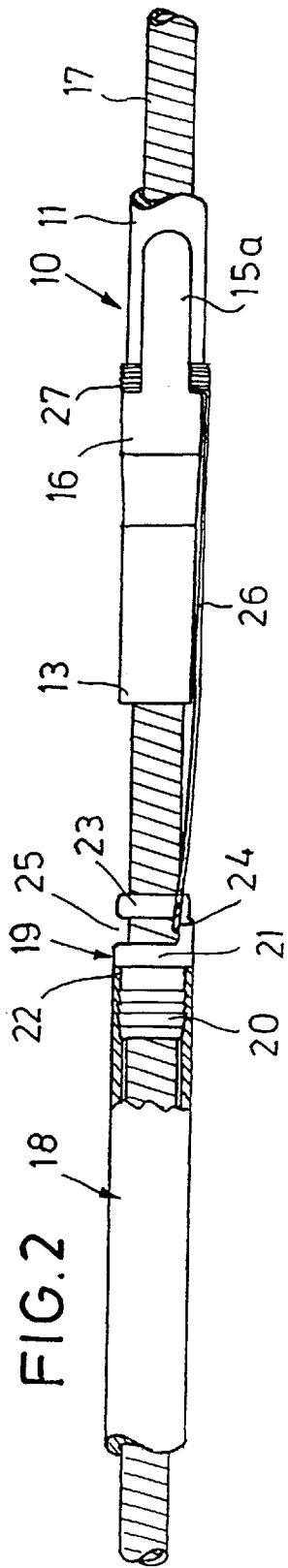
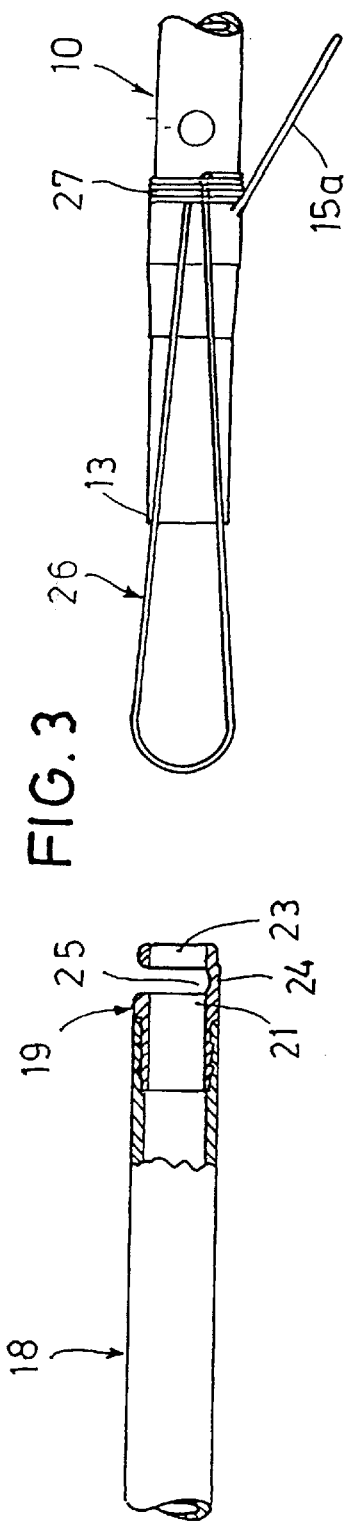

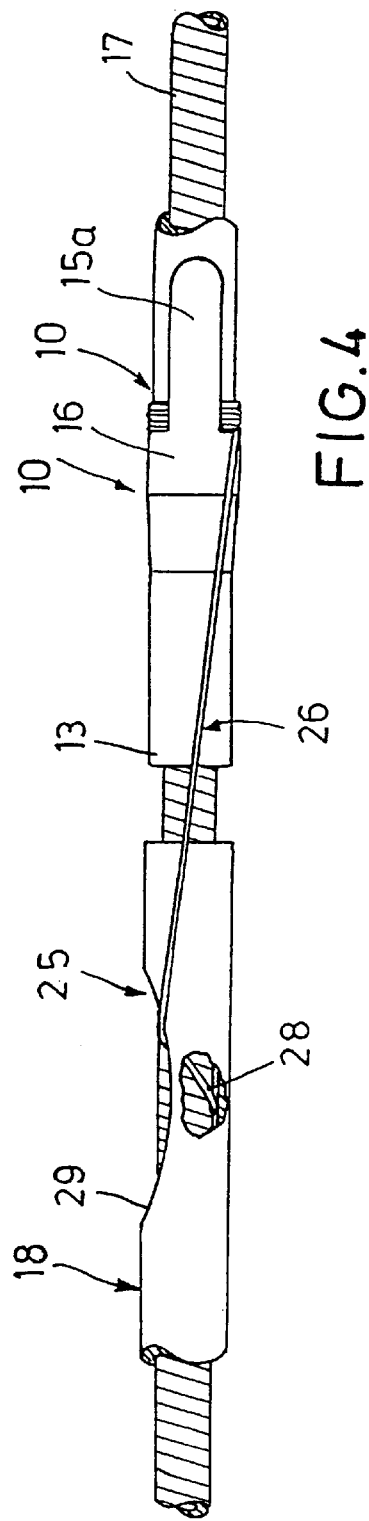
FIG.4
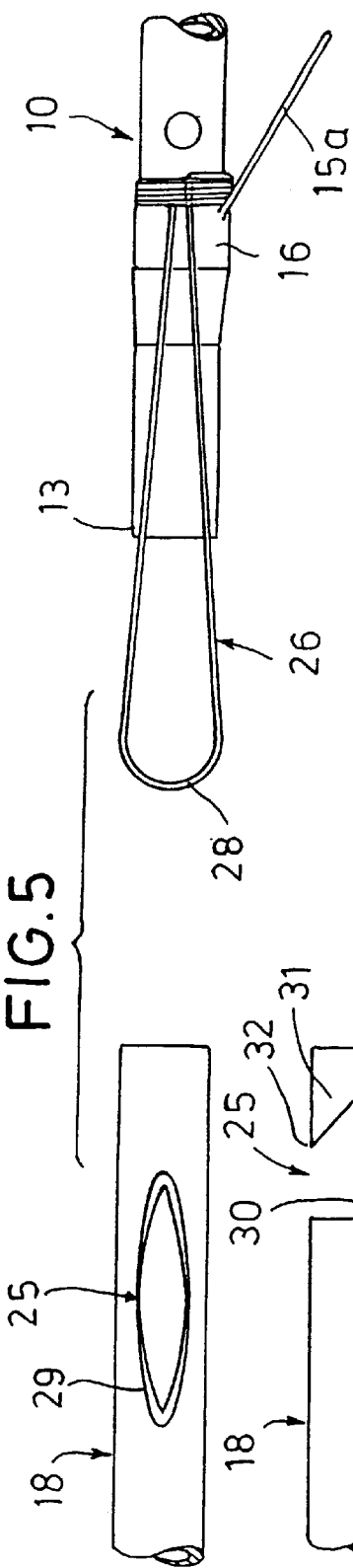
FIG.5
FIG.6

STENT ASSEMBLY

BACKGROUND OF THE INVENTION

The present invention relates to a stent assembly for keeping open body channels, especially the bile duct.

For draining body cavities, it is known to use a stent assembly, wherein a stent acting as a draining tube is introduced in a patient's body on a guiding string. U.S. Pat. No. 4,963,129 describes a stent assembly with a tubular stent for draining the cavity system of the kidneys. This stent is introduced via a guiding string which is withdrawn when the stent has been positioned. Moreover, a so-called pusher hose is pushed over the guiding string. The proximal end of the stent is supported at the distal end of the pusher hose. A coupling means is provided for transmitting not only thrust forces, but also tensile forces from the pusher hose to the stent. The coupling means consists of two complementary parts at the stent and at the pusher hose that mutually embrace each other and are locked by the guiding string passed therethrough such that they cannot be disengaged with the guiding string inserted. Thus, it is possible to position the stent very accurately, it being possible to pull back the stent over some distance before the disengagement.

German Patent DE 42 33 514 C1 describes a ureter catheter also placed over a guiding string, a pusher hose being provided in addition. The catheter and the pusher hose are connected through a disengageable coupling device locked by the guiding string.

A body channel that is especially hard to access is the bile duct. The bile duct leads the bile produced in the liver into the duodenum. At the mouth of the bile duct, a constriction is located that is called papilla or sphincter and functions as a valve. Liquid bile produced in the liver is introduced into the intestines through the bile duct. When the bile duct is clogged, a stent is introduced for keeping it open, the stent being a tubular prosthesis through which the liquid bile is introduced into the intestines. Inserting the stent is generally done with the help of a special endoscope from the distal end of which the stent is pushed out laterally. In doing so, it may happen that the stent is introduced to deep into the bile duct or is displaced after insertion and disappears in the bile duct. Further, it may happen that the stent becomes obstructed after having been placed. In such cases, it is necessary to remove the stent endoscopically or the correct its position.

SUMMARY OF THE INVENTION

It is the object of the invention to provide a stent assembly that is suitable for placement of the stent in a body channel, on the one hand,.and that, on the other hand, allows for later repositioning or extraction of the stent.

In the stent assembly of the present invention, the coupling device comprises a filament making the connection to the pusher hose. The coupling device is locked by means of the guiding string and unlocked when the guiding string is pulled out. In this context, a guiding string is a guiding wire or, in general, a guiding probe of plastic material, for example. In the unlocked state, the pusher hose may be withdrawn while the stent remains in the body channel. The filament is still located at the proximal end of the stent. Should it be found that the stent is positioned too far in the body channel, it may be pulled back by pulling at the filament. Thus, positional corrections can be made easily either immediately after the positioning of the stent or at a later time, using an instrument, e.g. having a pair of tongs for pulling at the filament, introduced into the body. It is also possible to remove the stent at a later time without any problems.

The present stent assembly is particularly suited for a bile duct stent. The bile duct is a body channel that is very difficult to access invasively. The filament at the proximal end of the stent is readily accessible from the duodenum after the placement of the stent and can thus be reached well from the intestines using a gripping instrument such as tongs.

The stent forms an elongated draining tube with a length of about 4–18 cm for bridging constrictions (stenoses) or occlusions, preferably in a bile duct. Suitably, the stent is provided with barbs to fix it. Such a barb and/or a sleeve carrying the barbs is suitably used as retaining elements for the filament. The filament has a typical length of about 2–10 cm.

Preferably, the filament forms a filament loop. This enables a simple and strong coupling with the pusher hose and a simple gripping for positional corrections with an instrument, e.g., having a hook.

BRIEF DESCRIPTION OF THE DRAWINGS

The following is a detailed description of the invention with reference to the accompanying drawings.

In the Figures:

FIG. 1 is a side elevational view of a stent for bile duct draining,

FIG. 2 is an enlarged side elevational view of the coupling site between stent and pusher hose, FIG. 3 is a representation of the ends of the stent and the pusher hose after withdrawal of the guiding string, FIG. 4 is a second embodiment of the stent assembly, FIG. 5 illustrates the ends of the stent and the pusher hose according to a second embodiment after removal of the guiding string, and FIG. 6 is a side elevational view of the end of a pusher hose according to a third embodiment.

DETAILED DESCRIPTION OF PREFERRED EMBODIMENTS

Referring now to the Figures, FIG. 1 illustrates a stent 10 for draining the bile duct. This stent is an elongate hose 11 of semi-rigid plastic material which is flexible yet has a high resistance against compression. The hose 11 has a length of approximately 4–18 cm and an inner diameter of at least 1 mm. The hose 11 is open at the distal end 12 and the proximal end 13. Near the distal end 12 holes 14 are provided in the sides and a further lateral hole 14 is located near the proximal end 13.

Further, the stent 10 comprises a plurality of barbs 15 slanted backward and each being supported by a circular sleeve 16 that closely surrounds the hose 11. The proximal end 13 is also provided with a sleeve 16 with a barb 15a, this barb, however, being slanted forward.

FIG. 2 illustrates the proximal end portion of the stent 10, a guiding string in the form of a guiding wire 17 being passed through the lumen of the stent. The guiding wire 17 helps with the introduction for implanting the stent. A pusher hose 18 is pushed onto the guiding wire 17, the distal end of the hose being adapted to push against the proximal end 13 of the stent 10 so as to displace the stent in the longitudinal direction relative to the guiding wire 17. Both the stent 10 and the pusher hose 18 are longitudinally displaceable on the guiding wire 17. At the distal end of the pusher hose 18, a coupling element 19 is provided that comprises a tubular sleeve 20 inserted into the pusher hose and a ring member 21 supported at the end 22 of the pusher hose 18. Another ring member 23 is arranged in parallel to and axially spaced from the ring member 21. The two ring members 21 and 23 are interconnected by an axial bridge 24. A receptacle 25 in the form of a slot open at the side is located between the ring members 21 and 23. This slot extends over a circumferential angle of more than 180°, preferably more than 270°, so that the bridge 24 occupies a circumferential angle of less than 90°.

A filament loop 26 is fastened at the stent 10. The loop comprises a filament winding 27 wound around the hose 11 below the barb 15a so that the barb prevents movement of the filament winding 27 towards the proximal end 13. Two loop legs extend from the filament winding 27 and form the closed filament loop 26. The filament loop 26 extends beyond the proximal end 13 of the stent 10.

According to FIG. 3, the filament loop 26 is first inserted from the side into the receptacle 25 at the pusher hose 18 until it meets the bridge 24. In this state, the stent and the pusher hose 18 are axially spaced from each other. Then, the guiding wire 17 is advanced through the pusher hose 18 and the stent 10 so that it assumes the position illustrated in FIG. 2. Thereby, the filament loop 26 is locked in the receptacle 25 by the guiding wire 17. The pusher hose 18 can be advanced relative to the guiding wire 27 so as to move the stent 10. Moreover, the pusher hose 18 may be withdrawn (to the left) taking along the stent via the filament loop 26.

After the stent 10 has been placed in the body channel, the guiding wire 17 is withdrawn from the stent 10 and the pusher hose 18. The filament loop 26 is released so that it can escape from the receptacle 25. Now, the filament loop 26 extends freely from the proximal end 13 of the stent 10. It may be grasped with a gripping instrument or a hook to withdraw the stent from the body channel, if need be.

In FIGS. 4 and 5, a second embodiment is illustrated wherein the receptacle 25 is a longitudinal opening 29 in the side wall of the pusher hose 18. Both loop legs of the filament loop 26 is placed into the opening 29 so that the sling 28 is within the pusher hose 18 where it is covered by the guiding wire 17. The sling 28 is located on the side of the lumen opposite the opening 29 and is locked by the guiding wire 17. After the guiding wire 17 has been withdrawn, the filament loop 26 is released so that the pusher hose 18 may be removed while the stent 10 remains at its position. The opening 29 has a width 29 extending over less than 180° of the circumference of the pusher hose and preferably over about 90°. The length of the opening 29 exceeds the width.

FIG. 6 illustrates the end of a pusher hose 18 according to a third embodiment. The stent (not illustrated) is configured as in the other two embodiments. In this case, the receptacle 25 is formed as a barb-like opening 30 in the pusher hose 18. In side elevational view, the opening 30 is wedge-shaped. Thus, a tongue-shaped barb 31 is formed in the pusher hose 18, the tip 32 of the barb being directed rearward in the axial direction away from the stent. The tongue starts at the outer edges of the opening 30 and converges in the middle to form the tip 32.

The filament loop (not illustrated) is first placed in the opening 30 so that it crosses the pusher hose 18. By pulling out the guiding wire, the filament loop is released, when the pusher hose 18 is advanced a little farther. The pusher hose 18 may also be used as a gripping hook for gripping and withdrawing the stent again. In this case, the filament loop of the stent slides downward along the inclined portion of the barb 31 so that the filament is drawn tight at the barb.

What is claimed is:

1. A stent assembly for keeping open body channels, in particular the bile duct, comprising:
   a tubular stent,
   a guiding string over which the stent may be pushed,
   a pusher hose adapted to be pushed over the guiding string for advancing the stent relative to the guiding string,
   and a coupling device for releasably connecting the stent with the hose,
wherein the coupling device has a filament fastened to the stent, said filament being insertable into a laterally open receptacle in the pusher hose and being blocked there by the inserted guiding string.

2. The stent assembly of claim 1, wherein the filament forms a filament loop.

3. The stent assembly of claim 1, wherein the receptacle is formed in a coupling element fastened at the pusher hose, wherein the receptacle is a transversely extending slot.

4. The stent assembly of claim 1, wherein the receptacle is formed at the pusher hose and has a longitudinally extending opening in the side wall of the pusher hose.

5. The stent assembly of claim 1, wherein an opening is formed in the pusher hose, which, in side elevational view, is shaped like a barb with a proximally directed tip.

6. The stent assembly of claim 1, wherein the stent has barbs at its circumference, and the barbs and/or the sleeve carrying the barb serve as a retaining element for the filament.

* * * * *